United States Patent
Davis et al.

(10) Patent No.: US 9,133,527 B2
(45) Date of Patent: Sep. 15, 2015

(54) **CELL WALL PROTEIN CWPV (CD0514) AS A DIAGNOSTIC MARKER FOR *CLOSTRIDIUM DIFFICILE* RIBOTYPE 027**

(71) Applicant: TECHLAB, INC., Blacksburg, VA (US)

(72) Inventors: Manli Y. Davis, Christiansburg, VA (US); Krista A. Williams, Blacksburg, VA (US); Jocelyn N. Browning, Blacksburg, VA (US); David M. Lyerly, Radford, VA (US)

(73) Assignee: TECHLAB, INC., Blacksburg, VA (US)

( * ) Notice: Subject to any disclaimer, the term of this patent is extended or adjusted under 35 U.S.C. 154(b) by 65 days.

(21) Appl. No.: 13/889,670

(22) Filed: May 8, 2013

(65) Prior Publication Data
US 2013/0302813 A1    Nov. 14, 2013

Related U.S. Application Data

(60) Provisional application No. 61/645,964, filed on May 11, 2012.

(51) Int. Cl.
| | |
|---|---|
| *G01N 33/53* | (2006.01) |
| *G01N 33/554* | (2006.01) |
| *C12Q 1/68* | (2006.01) |
| *G01N 33/569* | (2006.01) |

(52) U.S. Cl.
CPC .......... *C12Q 1/689* (2013.01); *G01N 33/56911* (2013.01)

(58) Field of Classification Search
CPC ...................................................... C12Q 1/689
See application file for complete search history.

(56) References Cited

U.S. PATENT DOCUMENTS

| | | |
|---|---|---|
| 2011/0020845 A1 | 1/2011 | Braun et al. |
| 2012/0276059 A1 | 11/2012 | Boone et al. |
| 2013/0130281 A1 | 5/2013 | Davis et al. |

OTHER PUBLICATIONS

Schroeder, M.S., *Clostridium difficile*-associated diarrhea. Am Fam Physician, 2005. 71(5): p. 921-8.
Aronsson, B., R. Mollby, and C.E. Nord, Antimicrobial agents and *Clostridium difficile* in acute enteric disease: epidemiological data from Sweden, 1980-1982. J Infect Dis, 1985 151(3): p. 476-81.
Zilberberg, M.D., et al., *Clostridium difficile*-associated disease and mortality among the elderly critically ill. Crit Care Med, 2009. 37(9): p. 2583-9.
Kim, K.H., et al., Isolation of *Clostridium difficile* from the environment and contacts of patients with antibiotic-associated colitis. J Infect Dis, 1981. 143(1): p. 42-50.
McGlone, S., et al., The economic burden of *Clostridium difficile*. Clin Microbiol Infect, 2011 18(3): p. 282-9.
Redelings M.D., F. Sorvillo, and L. Mascola, Increase in *Clostridium difficile*-related mortality rates, United States, 1999-2004. Emerg Infect Dis, 2007. 13(9): p. 1417-9.
Kuijper, E.J., et al., Update of *Clostridium difficile* infection due to PCR ribotype 027 in Europe, 2008. Euro Surveill, 2008. 13(31).
Tome, S., et al., Serotyping of *Clostridium difficile*. J Clin Microbial, 1988. 26(3): p. 426-8.
Rupnik, M., *Clostridium difficile* toxinotyping, Methods Mol Biol, 2010. 646: p. 67-76.
Alonso, R et al , An improved protocol for pulsed-field gel electrophoresis typing of *Clostridium difficile*. J Med Microbiol. 2005. 54(Pt 2): p. 155-7.
Stubbs, S.L., et al., PCR targeted to the 168-235 rRNA gene intergenic spacer region of *Clostridium difficile* and construction of a library consisting of 116 different PCR ribotypes. J Clin Microbiol, 1999. 37(21) p. 461-3.
McDonald, L.C., et al., An epidemic, toxin gene-variant rain of *Clostridium difficile*. N Engl J Med, 2005. 353(23): p. 2433-41.
Kuijper, E.J., B. Coignard, and P. Tull, Emergence of *Clostridium difficile*-associated disease in North America and Europe. Clin Microbiol Infect, 2006. 12 Suppl 6: p. 2-18.
Warny, M. et al., Toxin production by an emerging strain of *Clostridium difficile* associated with outbreaks of severe disease in North America and Europe. Lancet, 2005. 366(9491): p. 1079-84.
Dupuy, B., et al., *Clostridium difficile* toxin synthesis is negatively regulated by TcdC. J Med Microbiol, 2008. 57(Pt 6): p. 685-9.
Pepin, J., et al., Emergence of fluoroquinolones as the predominant risk factor for *Clostridium difficile*-associated diarrhea: a cohort study during an epidemic in Quebec. Clin Infect Dis, 2005. 41(9). p. 1254-60.
Schmidt. C., B. Loftier, and G. Ackermann, Antimicrobial phenotypes and molecular basis in clinical strains of *Clostridium difficile* Diagn Microbiol Infect Dis, 2007 59(1): p. 1-5.
Cartman, S.T., et al., The emergence of 'hypervirulence' in *Clostridium difficile*. Int J Med Microbiol, 2010. 300(6): p. 387-95.
Miller, M., et al., Healthcare-associated *Clostridium difficile* infection in Canada: patient age and infecting strain type are highly predictive of severe outcome and mortality. Clin Infect Dis, 2009. 50(2): p. 194-201.
Walker, A.S., et al., Relationship Between Bacterial Strain Type, Host Biomarkers and Mortality in *Clostridium difficile* Infection. Clin Infect Dis, 2013.
Skraban, J., et al., Gut Microbiota Patterns Associated with Colonization of Different *Clostridium difficile* Ribotypes. PLoS One, 2013 8(2): p. e58005.
Cloud, J., et al., *Clostirdium difficile* strain NAP-1 is not associated with severe disease in a nonepidemic settng. Clin Gastroenterol Hepatol, 2009. 7(8): p. 868-873 e2.
Sirard, S., L. Valiquette, and L.C. Fortier, Lack of association between clinical outcome of *Clostridium difficile* infections, strain type, and virulence-associated phenotypes. J Clin Microbiol; 2011. 49(12): p. 4040-6.
Walk, S. T., et al., *Clostridium difficile* ribotype does not predict severe infection. Clin Infect Dis, 2012. 55(12): p. 1661-8.
Gerding, D.N. and S. Johnson, Does infection with specific *Clostridium difficile* strains or clades influence clinical outcome? Clin Infect Dis, 2013.

(Continued)

*Primary Examiner* — Albert Navarro
(74) *Attorney, Agent, or Firm* — Shook, Hardy & Bacon L.L.P.

(57) ABSTRACT

Accurate and rapid differentiation of the outbreak strain ribotype 027 from other possible *Clostridium difficile* (*C. difficile*) strains, using stool samples, facilitates decision making for treatment options. Cell wall protein V (CwpV) contains a cell wall binding domain conserved among *C. difficile* strains and a variable domain which is antigenically different among *C. difficile* strains. In embodiments, antibodies against the 027-specific region in CwpV are used in diagnostic tests to detect ribotype 027 in culture or fecal samples.

7 Claims, 3 Drawing Sheets

(56) References Cited

OTHER PUBLICATIONS

Pepin, J., Vancomycin for the treatment of *Clostridium difficile* infection: for whom is this expensive bullet really magic? Clin Infect Dis, 2008. 46(10): p. 1493-8.

Credito, K.L. and P.C. Appelbaum, Activity of OPT-80, a novel macrocycle, compared with those of eight other agents against selected anaerobic species. Antimicrob Agents Chemother, 2004. 48(11): p. 4430-4.

Finegold, S.M., et al., In vitro activities of OPT-80 and comparator drugs against intestinal bacteria. Antimicrob Agents Chemother, 2004 48(12): p. 4898-902.

Louie, T.J., et al., OPT-80 eliminates *Clostridium difficile* and is sparing of Bacteroides species during treatment of *C. difficile* infection. Antimicrob Agents Chemother, 2009. 53(1): p. 261-3.

Biedenbach, D.J et al., In vitro activity of fidaxomicin (OPT-80) tested against contemporary clinical isolates of *Staphylococcus* spp. and *Enterococcus* spp. Antimicrob Agents Chemother, 2010. 54(5): p. 2273-5.

Whitman, C.B. and Q.A. Czosnowski, Fidaxomicin for the treatment of *Clostridium difficile* infections. Ann Pharmacother, 2012 46(2): p. 219-28.

Lancaster, J.W. and S.J. Matthews, Fidaxomicin: the newest addition to the armamentarium against *Clostridium difficile* infections. Clin Ther, 2012. 34(1): p. 1-13.

Baddour, L.M., Recurrent *Clostridium difficile* Infection: Enter Fidaxomicin. Journal Watch Infectious Diseases, 2012.

Kok, J., et al., Presumptive identification of *Clostridium difficile* strain 027/NAP1/BI on Cepheid Xpert: interpret with caution. J Clin Microbiol, 2011. 49(10): p. 3719-21.

Calabi, E., et al., Binding of *Clostridium difficile* surface layer proteins to gastrointestinal tissues. Infect Immun, 2002. 70(10): p. 5770-8.

Emerson, J.E., et al., A novel genetic switch controls phase variable expression of CwpV, a *Clostridium difficile* cell wall protein. Mol Microbiol, 2009. 74(3): p. 541-56.

Reynolds, C.B. et al., The *Clostridium difficile* cell wall protein CwpV is antigenically variable between strains, but exhibits conserved aggregation-promoting function. PLoS Pathog, 2011. 7(4): p. e1002024.

Boetzkes, A., et al., Secretome analysis of *Clostridium difficile* strains. Arch Microbiol, 2012.

Written Opinion of the International Searching Authority in PCT/US13/40399 mailed Sep. 13, 2013, 53 pages.

Reynolds, CB. et al. The *Clostridium difficile* Cell Wall Protein CwpV is Antigenically Variable Between Strains, but Exhibits Conserved Aggregation-Promoting Function. PLoS Pathogens. Apr. 21, 2011, vol. 7, No. 4; pp. 1-14. DOI: 10.1371/journal.ppat.1002024; entire document.

Dipersio, Jr et al. Development of a Rapid Enzyme Immunoassay for *Clostridium difficile* Toxin A and its Use in the Diagnosis of a *C. difficile*-Associated Disease. Journal of Clinical Microbiology. Dec. 1991, vol. 29, No. 12, pp. 2724-2730; entire document.

|  | PCR Ribotyping | |
| --- | --- | --- |
| N=72 | 027 | non-o27 |
| Anti-CwpV ELISA + | 30 | 5 |
| Anti-CwpV ELISA − | 5 | 32 |

*FIG. 1.*

| Ribotype | Reaction on anti-CwpV ELISA |
|---|---|
| 001 | - |
| 002 | - |
| 003 | - |
| 005 | - |
| 009 | - |
| 010 | - |
| 012 | - |
| 014 | - |
| 015 | - |
| 017 | - |
| 018 | - |
| 019 | - |
| 027 | + |
| 031 | - |
| 032 | - |
| 038 | - |
| 039 | - |
| 043 | - |
| 046 | - |
| 050 | - |
| 051 | - |
| 053 | - |
| 054 | - |
| 056 | - |
| 057 | - |
| 078 | - |
| 081 | - |
| 085 | - |
| 103 | - |
| 106 | - |
| 126 | - |
| 137 | - |
| 251 | - |
| 379 | - |

*FIG. 2.*

| N=195 | Tissue culture + | | Tissue culture - |
|---|---|---|---|
| | 027 by Ribotyping | non-027 by Ribotyping | |
| + on anti-CwpV QUIK CHEK | 10 | 0 | 0 |
| - on anti-CwpV QUIK CHEK | 2 | 10 | 173 |

CELL WALL PROTEIN CWPV (CD0514) AS A DIAGNOSTIC MARKER FOR *CLOSTRIDIUM DIFFICILE* RIBOTYPE 027

CROSS-REFERENCE TO RELATED APPLICATIONS

This application claims the priority to U.S. Provisional Patent Application No. 61/645,964 filed May 11, 2012, entitled "Cell Wall Protein CwpV (CD0514) as a Diagnostic Marker for *Clostridium Difficile* Ribotype 027",which is herein incorporated by reference.

BACKGROUND

*Clostridium difficile* (*C. difficile*) is the most common known cause of nosocomial diarrhea and accounts for about 3 million cases of diarrhea annually in the United Sates. The risk factors of *C. difficile* infection (CDI) include exposure to antibiotics, advanced age, and residence in hospitals or long-term care facilities. The symptoms of CDI range from mild diarrhea to pseudomembranous colitis and toxic megacolon. The average cost of treatment is about $10,000 per case. The mortality rate of CDI increased from 5.7 deaths per million population in 1999 to 23.7 deaths per million population in 2004 due to the emergence of hypervirulent outbreak strains. The ribotype 027 strain contributed significantly to the increased CDI incidence. The accurate differentiation of the outbreak strain ribotype 027 from other strains of *C. difficile* can facilitate decision making for treatment options.

BRIEF DESCRIPTION OF THE DRAWINGS

Illustrative embodiments of the invention are described in detail below with reference to the attached drawing figures, wherein:

FIG. 1 depicts a comparison between anti-CwpV ELISA and PCR ribotyping methods, according to embodiments of the invention;

FIG. 2 depicts that antibodies generated against the 027-specific region of CwpV only recognize *C. difficile* ribotype 027, according to embodiments of the invention;

DETAILED DESCRIPTION

Figures 3, 4:
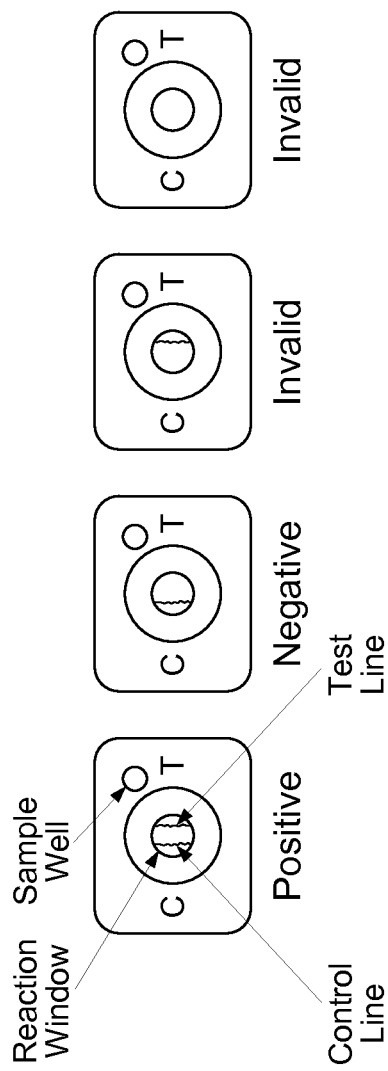
FIG. 3 depicts interpretation of the results of Anti-CwpV QUIK CHEK®.
FIG. 4 depicts a comparison between anti-CwpV QUIK CHEK® and PCR ribotyping methods, according to embodiments of the invention.

Embodiments of the present invention are directed to test methods for differentiating *C. difficile* strains in patients based on the presence of a ribotype specific new antigen marker, Cell Wall Protein V (CwpV). Ribotype specific CwpV may be used in an immunoassay for the detection of *C. difficile* ribotypes, especially the outbreak strain 027. In embodiments, anti-strain specific CwpV antibodies are used in immunoassays for highly sensitive identification of *C. difficile* strain 027.

Several typing methods have been developed in order to study the genetic relatedness among *C. difficile* strains and the association between the *C. difficile* strains and disease severity. These methods include serotyping, toxinotyping, pulse-field gel electrophoresis (PFGE) and PCR ribotyping. PCR ribotyping is relatively easy to perform, reproducible, and is one of the most discriminatory methods to differentiate *C. difficile* strains.

Starting in the late 90's a 5-fold increase of CDI has been observed and it is suspected that the spread of a hypervirulent strain contributed to the outbreak. This outbreak strain was characterized as toxinotype III, North American pulse field gel electrophoresis type 1 (NAP1), restriction endonuclease analysis group I (BI) and PCR ribotype 027. Several characteristics of ribotype 027 contribute to the enhanced virulence of ribotype 027 strains. Besides toxins A and B, 027 strains express an additional binary toxin which may contribute to the severity of disease. 027 strains also contain an 18-base pair deletion and a frameshift mutation in the tcdC gene, which is the repressor of toxin production. The frameshift mutation may cause an increase of toxin production. The historical 027 strains isolated in France in 1988 were susceptible to fluoroquinolones and erythromycin but the mutations in gyrA/B and the 23s RNA genes rendered ribotype 027 in recent outbreaks resistance to both antibiotics. The altered surface proteins with higher affinity to human intestinal epithelial cells may also contribute to the enhanced virulence.

Infections with 027 strains were associated with more severe outcomes in some studies. The dramatic alteration of gut microbiota by the 027 strain is likely to contribute to its high pathogenicity. However, other studies indicated the lack of correlation between the ribotype of the infecting strain and the outcome of patients. The controversies might have resulted from the population studied and the methods used in statistical analysis.

The traditional antibiotics of choice for the treatment of CDI are metronidazole and vancomycin. For patients with mild-to-moderate CDI, metronidazole and vancomycin are equally effective. For patients with severe CDI caused by non-027 strains, vancomycin produced better outcomes. A high relapse rate was observed in patients treated with either metronidazole or vancomycin. In May 2010, a new drug named Fidaxomicin (Dificid; Optimer Pharmaceuticals) was approved by the U.S. Food and Drug Administration (FDA) for the treatment of *C. difficile*-associated diarrhea in adults. Fidaxomicin is a narrow spectrum antibiotic against gram-positive anaerobes. Resistance to fidaxomicin was found in *Bacteroides* spp., aerobic and facultative gram-negative bacilli and anaerobic gram-negative bacilli. Fidaxomicin is equally effective against 027 and non-027 strains of *C. difficile*. The use of broad-spectrum antibiotics disturbs the gut flora which may contribute to the relapse of *C. difficile* infection. Recent studies indicate that fidaxomicin treatment resulted in lower relapse rate in patients infected by non-027 strains in comparison to vancomycin treatment. Therefore the differentiation between 027 and non-027 strains may facilitate the decision making of the physicians in terms of treatment options.

The PCR ribotyping method requires the isolation of *C. difficile* colonies, DNA isolation from culture originated from pure colonies, DNA amplification by PCR, and gel electrophoresis. The complicated and time-consuming procedure is not practical in clinical labs. Commercially available molecular tests utilize the sequence variation in the tcdC gene. The PCR based tests are expensive and non-specific because the mutations in tcdC gene are also present in other ribotypes. Antibody-based tests, such as Enzyme-linked immunosorbent assays (ELISAs) and lateral flow assays, are rapid and cost-effective tests for the detection of pathogen-specific antigens. In embodiments, 027 strain specific antigen(s) are used as a diagnostic marker(s) for the detection of 027 strains in immunoassays.

*C. difficile* cells possess a surface layer (S-layer) outside of the peptidoglycan layer. The S-layer is present in both vegetative cells and *C. difficile* spores. Proteins within the S-layer mediate host-pathogen interactions. Several *C. difficile* surface proteins bind to gastrointestinal tissues and are potential colonization factors. The proteins associated with the S-layer contain two domains: a conserved cell wall binding domain and a variable domain that specifies the function of that particular protein. Twenty-eight cell wall proteins (CWPs) are predicted in the genome of the sequenced strain 630. The variable domains of certain CWPs are considered potential antigen markers for *C. difficile* strain identification.

CwpV (CD0514) is a member of the CWPs and consists of an N-terminal region with a putative cell wall binding domain and a C-terminal domain which may promote aggregation. CwpV is secreted into culture medium by various 027 strains. The C-terminal domain of CwpV is highly variable among *C. difficile* ribotypes. The specific amino acid sequences of the C-terminal repeats found in the CwpV protein in ribotype 027 are not represented in the genome of any other sequenced strains to date. In embodiments, the ribotype-specific region of CwpV can be used as a diagnostic marker for the 027 strains.

The following are examples of procedures which have been utilized to establish the preferred assays according to embodiments of the present invention. The following examples are merely exemplary and not presented by way of limitation.

EXAMPLE 1

A ribotype 027-specific C-terminal peptide of CwpV was expressed in *E. coli* using recombinant DNA techniques. Polyclonal antibodies against the recombinant CwpV were generated in goats. An ELISA was developed using polyclonal anti-CwpV antibodies as capturing antibodies and horseradish peroxidase (HRP)-conjugated polyclonal anti-CwpV antibodies as detection antibodies.

Seventy-two (72) clinical human fecal samples that were positive for *C. difficile* were tested using this anti-CwpV ELISA. The sensitivity and specificity of the anti-CwpV ELISA for detection of *C. difficile* 027 strains were calculated using the PCR ribotyping method as the gold standard. The cutoff of this ELISA was set to be an absorbance of 0.080 read on dual wavelength (OD450/620 nm).

Results

With reference to FIG. 1, the results of anti-CwpV ELISA on 72 human fecal samples were compared to the results of PCR ribotyping method. Anti-CwpV ELISA detected the presence of *C. difficile* 027 strain in 30 of the 35 027-positive samples determined by the PCR ribotyping method. The sensitivity and specificity of the anti-CwpV ELISA are each 86%.

EXAMPLE 2

A ribotype 027-specific C-terminal peptide of CwpV was expressed in *E. Coli*. Polyclonal antibodies against the recombinant CwpV were generated in goats. An ELISA was developed using polyclonal anti-CwpV antibodies as capturing antibodies and horseradish peroxidase (HRP)-conjugated polyclonal anti-CwpV antibodies as detection antibodies.

Thirty-four (34) *C. difficile* strains were inoculated into Brain-heart infusion broth (BHI; Oxoid). Cultures were grown at 37° C. overnight under anaerobic conditions. The *C. difficile* strains in BHI cultures were diluted 1:20 in phosphate buffered saline (PBS) and tested on the ELISA described above.

Results

As shown in FIG. 2, *C. difficile* cultures representing thirty-four (34) different ribotypes were tested on anti-CwpV ELISA using anti-027-specific antibodies. Ribotype 027 strain was the only ribotype that was detected on this ELISA. The thirty-three (33) non-027 *C. difficile* cultures were not detected by this ELISA. The cutoff of this ELISA was set to be an absorbance of 0.080 read on dual wavelength (OD450/620 nm).

EXAMPLE 3

A ribotype 027-specific C-terminal peptide of CwpV was expressed in *E. Coli*. Polyclonal antibodies against the recombinant CwpV were generated in goats. A QUIK CHEK® device was developed using polyclonal anti-CwpV antibodies immobilized as the test line on microfiber glass membrane as capturing antibodies and horseradish peroxidase (HRP)-conjugated polyclonal anti-CwpV antibodies as detection antibodies. Rabbit anti-HRP polyclonal antibodies were immobilized on the microfiber glass membrane to form a positive control line.

One hundred ninety-five (195) samples were tested using this anti-CwpV QUIK CHEK®. Clinical fecal samples were diluted in sample diluent, mixed with HRP-conjugated polyclonal anti-CwpV antibodies and applied to the microfiber glass membrane with immobilized capturing antibodies through the sample well. The sample-conjugate mixture flowed across the microfiber glass membrane through capillary action. The device was incubated at room temperature for fifteen (15) minutes to allow the capture of CwpV antigen in the samples by the immobilized anti-CwpV antibodies on the test line. The excess HRP-conjugated polyclonal anti-CwpV antibodies were captured by the immobilized rabbit anti-HRP antibodies on the control line. Following a quick wash of the membrane and the addition of HRP substrate through the reaction window, the device was incubated at room temperature for ten minutes before the results were recorded.

With reference to FIG. 3, a positive result on anti-CwpV QUIK CHEK® is indicated by two blue lines: the control line ("C") and the test line ("T"). A negative result on anti-CwpV QUIK CHEK® is indicated by a single blue line on the control ("C") side of the reaction window with no test line visible on the "T" side of the reaction window. The result is interpreted invalid when no control line ("C") is visible.

Results

One hundred and ninety-five (195) fecal samples were tested on the anti-CwpV QUIK CHEK®, tissue culture cytotoxicity assay, and the ribotypes of *C. difficile* isolated from samples containing toxigenic *C. difficile* were determined by PCR ribotyping method. As shown in FIG. 4, among the 195 fecal samples tested, one hundred seventy-three (173) samples were determined not to contain toxigenic *C. difficile* by tissue culture cytotoxicity assay. All of the samples that were negative by tissue culture method were negative on anti-CwpV QUIK CHEK®. Among the twenty-two (22) samples determined to contain *C. difficile* by the tissue culture cytotoxicity method, twelve (12) were identified as ribotype 027 by PCR ribotyping. Ten (10) out of the 12 samples showed a positive reaction when on anti-CwpV QUIK CHEK®. None of the non-027 *C. difficile* samples were detected by the anti-CwpV QUIK CHEK®. Using PCR ribotyping method as the gold standard, the sensitivity and specificity of anti-CwpV QUIK CHEK® were calculated to be 83% and 100%, respectively.

In summary, embodiments of the present invention provide CwpV as a diagnostic marker for detecting *C. difficile* ribotype 027 in stool samples and in cultures. The present invention has been described in relation to particular embodiments which are intended in all respects to be illustrative rather than restrictive. Alternative embodiments will become apparent to those skilled in the art to which the present invention pertains without departing from its scope.

From the foregoing, it will be seen that this invention is well adapted to attain all the ends and objects herein above set forth together with other advantages which are obvious and which are inherent to the method. It will be understood that certain features and subcombinations of the invention are of utility and may be employed without reference to other features and subcombinations. This is contemplated by and is within the scope of the claims.

What is claim is:

1. A method of diagnosing a patient with a ribotype 027 *C. difficile* strain infection that is associated with severe *C. difficile* infection, the method comprising:
    obtaining a fecal sample from a patient;
    determining that the patient has a *C. difficile* infection; and
    determining whether the patient has a ribotype 027 *C. difficile* strain infection by determining a presence of a ribotype 027-specific CwpV antigen in the fecal sample using an immunoassay against the CwpV antigen.

2. The method of claim 1, wherein the immunoassay is an enzyme-linked immunosorbent assay (ELISA) or an immunochemical reaction on a membrane, or a lateral flow assay.

3. The method of claim 1, wherein the immunoassay utilizes one or more of monoclonal, polyclonal or recombinant anti-ribotype 027-specific CwpV antibodies as capturing antibodies.

4. The method of claim 1, wherein the immunoassay utilizes HRP-conjugated polyclonal or monoclonal anti-ribotype 027-specific CwpV antibodies as detection antibodies.

5. The method of claim 1, wherein the immunoassay comprises one or more antibodies against CwpV raised against native CwpV produced by *C. difficile* or CwpV derived by recombinant DNA expression in *E. coli*.

6. The method of claim 1, wherein determining the presence of the ribotype 027 *C. difficile* further comprises identifying the presence of a DNA fragment encoding ribotype 027-specific CwpV using nucleic acid amplification assays.

7. The method of claim 1, further comprising diluting the fecal sample to create a diluted fecal sample; and using the diluted fecal sample in the immunoassay against the CwpV antigen.

* * * * *